United States Patent [19]

Budge et al.

[11] Patent Number: 5,473,086

[45] Date of Patent: Dec. 5, 1995

[54] PROCESS FOR THE HYDROGENATION OF MALEIC ACID TO 1,4-BUTANEDIOL

[75] Inventors: John R. Budge, Beachwood; Thomas G. Attig, Aurora, both of Ohio; S. Erik Pedersen, Hurricane, W. Va.

[73] Assignee: The Standard Oil Co., Cleveland, Ohio

[21] Appl. No.: 373,666

[22] Filed: Jan. 17, 1995

[51] Int. Cl.$^6$ .................................................. C07D 307/02
[52] U.S. Cl. ........................................... 549/509; 568/862
[58] Field of Search .............................. 568/862; 549/509

[56] References Cited

U.S. PATENT DOCUMENTS

| | | | |
|---|---|---|---|
| 3,948,805 | 4/1976 | Michalczyk et al. | 252/447 |
| 4,096,156 | 6/1978 | Freudenberger et al. | 260/343.6 |
| 4,550,185 | 10/1985 | Mabry et al. | 549/508 |
| 4,609,636 | 9/1986 | Mabry et al. | 502/183 |
| 4,985,572 | 1/1991 | Kitson et al. | 549/326 |

FOREIGN PATENT DOCUMENTS 1534232  11/1978  United Kingdom.
1551741  8/1979  United Kingdom.

*Primary Examiner*—C. Warren Ivy
*Assistant Examiner*—Amelia Owens
*Attorney, Agent, or Firm*—David P. Yusko; Michael F. Esposito; David J. Untener

[57] ABSTRACT

Maleic acid, maleic anhydride or other hydrogenatable precursor are catalytically hydrogenated to 1,4-butanediol and tetrahydrofuran. It has been discovered that high yields of 1,4-butanediol are achieved when the hydrogenation catalyst comprises palladium, silver and rhenium on a carbon support and is prepared by the steps of (i) impregnating a carbon support with a source of palladium, silver and rhenium, wherein the source of palladium, silver and rhenium is at least one solution, (ii) after each impregnation step, drying the impregnated carbon support to remove solvent, (iii) heating the impregnated carbon support at a temperature of about 120° C. to about 350° C. under reducing conditions. The palladium in the catalyst is present in the form of crystallites having a particle size of less than 10 nm.

16 Claims, No Drawings

PROCESS FOR THE HYDROGENATION OF MALEIC ACID TO 1,4-BUTANEDIOL

BACKGROUND OF THE INVENTION

1. Field of the Invention

This invention relates to an improved process for the hydrogenation of maleic acid, maleic anhydride or other hydrogenatable precursor to 1,4-butanediol and tetrahydrofuran. The process is characterized by the use of a catalyst comprising palladium, silver and rhenium on a carbon support. The process is also characterized by high yields of 1,4-butanediol with minimal formation of by-product gamma-butyrolactone.

2. Description of the Prior Art

It is well known that tetrahydrofuran, gamma-butyrolactone and 1,4-butanediol are obtained by the catalytic hydrogenation of maleic anhydride and related compounds. Tetrahydrofuran is a useful solvent for natural and synthetic resins and is a valuable intermediate in the manufacture of a number of chemicals and plastics. Gamma-butyrolactone is an intermediate for the synthesis of butyric acid compounds, polyvinylpyrrolidone and methionine. Gamma-butyrolactone is a useful solvent for acrylate and styrene polymers and also a useful ingredient of paint removers and textile assistants. 1,4-butanediol (a.k.a. 1,4-butylene glycol) is useful as a solvent, a humectant, an intermediate for plasticizers and pharmaceuticals, a cross-linking agent for polyurethane elastomers, a precursor in the manufacture of tetrahydrofuran, and is used to make terephthalate plastics.

Of particular interest in the instant invention are hydrogenation catalysts comprising palladium, silver and rhenium on a carbon support, which are useful for the hydrogenation of maleic anhydride, maleic acid and related compounds to tetrahydrofuran, gamma-butyrolactone and 1,4-butanediol.

British Patent No. 1,534,232 teaches the hydrogenation of carboxylic acids, lactones or anhydrides using a hydrogenation catalyst consisting of palladium and rhenium on a carbon support. U.S. Pat. Nos. 4,550,185 and 4,609,636 teach a process of making tetrahydrofuran and 1,4-butanediol by hydrogenating maleic acid, maleic anhydride or other hydrogenatable precursor in the presence of a catalyst comprising palladium and rhenium on a carbon support wherein the palladium and rhenium were present in the form of crystallites having an average palladium crystallite size of about 10 to 25 nm and an average rhenium crystallite size of less than 2.5 nm. The preparation of this catalyst is characterized by the deposition and reduction of the palladium species on the carbon support followed by the deposition and reduction of the rhenium species on the palladium impregnated carbon support.

U.S. Pat. No. 4,985,572 teaches a process for the catalytic hydrogenation of a carboxylic acid or an anhydride thereof to the corresponding alcohol and/or carboxylic acid ester using a catalyst comprising rhenium, palladium and silver on a carbon support. The preparation of this catalyst is characterized by the simultaneous deposition of palladium and silver on the carbon support followed by a high temperature (600° C.) heat treatment. Rhenium was then deposited on the palladium/silver impregnated carbon support. The resulting catalyst was then reduced.

Generally, in the hydrogenation of maleic acid, maleic anhydride or other hydrogenatable precursor the above discussed catalyst has the propensity to produce more tetrahydrofuran and gamma-butyrolactone than 1,4-butanediol. An object of this invention is a process and a catalyst which will maximize 1,4-butanediol production and minimize gamma-butyrolactone production.

SUMMARY OF THE INVENTION

Maleic acid, maleic anhydride or other hydrogenatable precursor are catalytically hydrogenated to 1,4-butanediol and tetrahydrofuran. It has been discovered that high yields of 1,4-butanediol are achieved when the hydrogenation catalyst comprises palladium, silver and rhenium on a carbon support and is prepared by the steps of (i) impregnating a carbon support with a source of palladium, silver and rhenium, wherein the source of palladium, silver and rhenium is at least one solution (i.e. one or more solutions), (ii) after each impregnation step, drying at a temperature under about 150° C. the impregnated carbon support to remove solvent, (iii) heating the impregnated carbon support at a temperature of about 100° C. to about 350° C. under reducing conditions.

In the resulting catalyst, palladium is present in the form of crystallites having an average particle size of less than 10 nm.

DETAILED DESCRIPTION OF THE INVENTION

A hydrogenatable precursor is catalytically hydrogenated to provide high yields of 1,4-butanediol and smaller yields of tetrahydrofuran with minimal gamma-butyrolactone formation.

Reactants

At least one hydrogenatable precursor is reacted with a hydrogen containing gas in the presence of the catalyst.

As used herein a "hydrogenatable precursor" is any carboxylic acid or anhydride thereof, carboxylic acid ester, lactone or mixture thereof which when hydrogenated produces 1,4-butanediol. Representative hydrogenatable precursors include maleic acid, maleic anhydride, fumaric acid, succinic anhydride, succinic acid, dimethyl succinate, gamma-butyrolactone or mixtures thereof. The preferred hydrogenatable precursors are maleic acid, maleic anhydride, succinic acid, succinic anhydride or mixtures thereof.

The most preferred hydrogenatable precursor is maleic acid which is typically obtained by reacting n-butane or benzene in an oxygen-containing gas in the presence of a catalyst to oxidize in the vapor phase the n-butane or benzene to maleic anhydride, and then collecting the maleic anhydride by a water quench to produce maleic acid in an aqueous solution. The oxidation of n-butane or benzene is typically operated at a temperature of about 300° C. to 600° C. and a pressure of about 0.5 to 20 atmospheres (50 to 2000 kPa).

Typically, the hydrogen ($H_2$) containing gas is commercially pure hydrogen with no diluent gases. However, the hydrogen containing gas in addition to hydrogen ($H_2$) may also contain nitrogen (N2), any gaseous hydrocarbon (e.g. methane), as well as gaseous oxides of carbon, (e.g. carbon monoxide, carbon dioxide).

Catalyst

The catalyst employed in the instant invention comprises palladium, silver and rhenium supported on carbon. The carbons for use in this invention have a BET surface area of at least 200 m$^2$/g, and preferably be in the range of 500–1500 m$^2$/g.

The catalyst composition comprises about 0.1 to about 20 weight percent palladium, preferably about 2 to about 8 weight percent palladium; about 0.1 to about 20 weight percent silver, preferably about 1 to about 8 weight percent silver; and about 0.1 to about 20 weight percent rhenium, preferably about 1 to about 10 weight percent rhenium. The ratio of palladium to silver is between 10 to 1 and 1 to 10. The catalyst composition may also be further modified through the incorporation of a metal or metals selected from Groups IA or IIA.

The catalysts of this invention may be conveniently prepared by impregnation of the carbon support, either in single or multiple impregnation steps, with a solution or solutions containing at least one palladium, silver or rhenium compound. As used herein, impregnation of the carbon support means to cause the carbon support to be filled, imbued, permeated, saturated or coated. The impregnating solution may optionally contain complexing agents to help solubilize one or more of the metal compounds. The catalyst is dried after each impregnation step to remove any carrier solvent. Drying temperatures are between about 80° C. and about 150° C.

The solutions of palladium compound, silver compound and rhenium compound can be applied to the carbon by immersing or suspending the support material in the solution or by spraying the solution onto the carbon. The solution containing the palladium compound is typically an aqueous solution containing an amount of palladium compound to yield a catalyst product with the requisite amount of palladium. The palladium compound may be palladium nitrate or a palladium compound such as a chloride, carbonate, carboxylate, acetate, acetyl acetonate, or amine. The solution containing the silver compound is typically an aqueous one containing an amount of silver compound to yield a catalyst product with the requisite amount of silver. The palladium and silver compounds should be thermally decomposable and reducible to the metals. The solution containing the rhenium compound is typically an aqueous one containing an amount of rhenium compound to yield a catalyst product with the requisite amount of rhenium. The rhenium compound is typically perrhenic acid, ammonium perrhenate or an alkali metal perrhenate.

After impregnation with palladium, silver and rhenium and drying, the catalyst is activated by heating the impregnated carbon support under reducing conditions at a temperature of 120°–350° C., preferably 150°–300° C. Hydrogen, or a mixture of hydrogen and nitrogen, in contact with the catalyst may be conveniently used for the catalyst reduction. Reduction of the impregnated carbon support is only after the carbon support has been impregnated with palladium, silver and rhenium. In the case of multiple impregnation steps and multiple dryings, the reduction of the catalyst is done after the final drying.

The palladium in catalysts of the present invention is present in the form of crystallites having an average crystallite size of less than 100 angstroms (10 nm). More specifically, when freshly reduced samples of the palladium/silver/rhenium on a carbon support as used herein are analyzed by X-ray diffraction (XRD) and Scanning Transmission Electron Microscopy (STEM), the palladium containing particles (i.e. particles of palladium or of palladium and silver) in the catalyst are finely dispersed and have a very small crystallite size of less than about 50 angstroms (5 nm). The rhenium is very finely dispersed such that particles of rhenium are not detectable by XRD or STEM. Using STEM analysis the average palladium containing particle crystallite size is calculated to be less than 34 angstroms (3.4 nm). As used herein the "particle size distribution" and "mean particle size" are as defined in "Structure of Metal Catalysts" by J. R. Anderson, pages 358–359, Academic Press (1975), which is incorporated herein by reference.

Lastly the preparation of the catalysts described herein does not employ large amounts of excess water which must be removed during the drying step nor does it employ a high temperature (i.e. about 600° C.) treatment step as taught in U.S. Pat. No. 4,985,572.

The Process

The method for carrying out the process comprises reacting a hydrogenatable precursor with a hydrogen-containing gas in the presence of the hydrogenation catalyst, and recovering and purifying the reaction products by distillation.

The liquid phase hydrogenation of this invention can be run using conventional apparatus and techniques in a stirred-tank reactor or in a fixed-bed reactor. Single or multiple-stage reactors may be employed. The amount of catalyst required will vary widely and is dependent upon a number of factors such as reactor size and design, contact time and the like.

The hydrogen-containing gas is fed continuously, generally with the hydrogen in considerable stoichiometric excess to the other reactants. Unreacted hydrogen can be returned to the reactor as a recycle stream. The precursor solution, e.g., maleic acid solution, is fed continuously at concentrations ranging from dilute solutions to near the maximum solubility level, typically about 30 to about 50 weight percent.

Preferably the hydrogenation step is run at a temperature of about 50° C. to 350° C., and a hydrogen pressure of about 20–400 atmospheres with hydrogen to hydrogenatable precursor ratios (H$_2$/P) of between 5 to 1 and 1000 to 1 and contact times of 0.1 minute to 20 hours.

The reaction products, 1,4-butanediol, tetrahydrofuran, gamma-butyrolactone or mixtures thereof, are advantageously separated by fractional distillation. By-products which are formed in small amounts or unreacted feed, such as for example, succinic anhydride or succinic acid, are optionally returned to the hydrogenation stage. The gamma-butyrolactone may also be recycled to the hydrogenation reactor.

Using the process of this invention, more specifically using the hydrogenation catalyst described herein, maleic acid is converted virtually quantitatively in a simple reaction. The yields of 1,4-butanediol and tetrahydrofuran achieved are about 80 mole percent or greater, typically about 90 mole percent or greater, with a majority portion of the yield being 1,4-butanediol. Reaction by-products may include n-butanol, n-butyric acid, n-propanol, propionic acid, methane, propane, n-butane, carbon monoxide, and carbon dioxide. However, the formation of non-utilizable by-products is slight.

SPECIFIC EMBODIMENTS

In order to illustrate the instant invention the following examples are provided.

Example 1—Catalyst Preparation—3.5 wt % Pd/3.5 wt % Ag/5.3 wt % Re/C Catalyst A catalyst was prepared having approximately 3.5 weight percent Pd, 3.5 weight percent Ag and 5.3 weight percent Re on an activated carbon support (ACL 40, produced by CECA S.A. of France and sold in the United States by Atochem North America Inc.). This support was obtained in 1.5 mm extrude form and was ground and sieved to give a 30 to 70 mesh fraction. The catalyst was prepared by impregnating the carbon support with a solution comprising palladium, silver and rhenium.

Specifically Pd/Ag/Re solution was prepared as follows: 109.8 g of palladium nitrate solution (7.26% Pd), 14.6 g of silver nitrate, and 27 g of perrhenic acid solution (52% Re), were placed in a 250 c.c. volumetric flask and acetonitrile was added to bring the solution volume up to the mark. The weight of the solution was 273.96 g.

198g of the 30/70 mesh ACL40 was impregnated with 253.7 g of the Pd/Ag/Re solution and allowed to stand for 4 hours. The catalyst was then dried at 120° C. in an oven overnight.

Using STEM analysis, this catalyst (after reduction as set forth in Example 2) had a palladium containing particle crystallite size of 3.4 nm.

Comparative Example A—3.6 wt % Pd/5.5 wt % Re/C Catalyst

A catalyst having approximately 3.6 weight percent Pd and 5.5 weight percent Re on the 30/70 mesh ACL40 was prepared similar to Example 1.

Specifically, a Pd/Re solution was prepared as follows: 11.86 g of palladium nitrate solution (7.26% Pd) and 2.7 g of perrhenic acid solution (52% Re) were placed in a 25 c.c. volumetric flask and acetonitrile was added to bring the solution volume up to the mark. The weight of the solution was 26.63 g.

19.8 g of the 30/70 mesh ACL40 was impregnated with 24.7 g of the Pd/Re solution and allowed to stand for 4 hours. The catalyst was then dried at 120° C. in an oven overnight.

XRD analysis of this catalyst (after reduction as set forth in Example 2) showed no diffraction peaks, indicating that there were not a significant number of palladium containing particles larger than 5 nm.

Example 2—Catalyst Testing 38 c.c. of the Pd/Ag/Re/C catalyst prepared in Example 1 was charged to a 0.5" O.D. Hastelloy C276 reactor. The catalyst was then reduced at atmospheric pressure with 0.5 SLM of $H_2$ flowing over the catalyst, with the following time/temperature profile: room temperature to 280° C. over 11 hours, and then held at 280° C. for 5 hours.

Catalyst testing was carried out at 1300 psig and 180° C. (Average Set Temperature) using a 35.5 weight percent maleic acid/64.5 weight percent $H_2O$ feed. Over an approximately 30 hour period, the $H_2$ GHSV and MAC LHSV were gradually increased from 2097 to 3021 $h^{-1}$, and 0.38 to 0 55 $h^{-1}$, respectively.

Table 1 summarizes the process parameters and product selectivities obtained after 47 hours on stream.

For comparison 38 c.c. of the catalyst Pd/Re/C prepared as in Comparative Example A was tested as described above. The results are summarized in Table 1.

Table 1 illustrates that the Pd/Ag/Re/C catalyst of the instant invention is a more active catalyst than the non-silver containing catalysts known in the art. Specifically the Pd/Ag/Re/C catalyst produced more 1,4-butanediol and much less gamma-butyrolactone or other reaction products as the Pd/Re/C catalyst.

Example 3—3.3 wt % Pd/3.2 wt % Ag/6.6 wt % Re/C Catalyst Preparation

A catalyst having approximately 3.3 weight percent Pd, 3.2 weight percent Ag and 6.6 weight percent Re on the ACL40 carbon support was prepared as follows: 130.25 g of palladium nitrate solution (7.7% Pd), 16.5 g of silver nitrate, and 41.5 g of perrhenic acid (52.6% Re), were placed in a 250 c.c. volumetric flask. Acetonitrile was added and the mixture shaken to dissolve the solids. The solution was made up to the mark with acetonitrile. The weight of the solution was 296.2 g.

TABLE 1

| | | | MALEIC ACID HYDROGENATION | | | | | | | | |
|---|---|---|---|---|---|---|---|---|---|---|---|
| | TOS | Press. | | Temp# | GHSV | LHSV | | Selectivity | | | |
| Catalyst | (h) | (psig) | [MAC] | (°C.) | ($h^{-1}$) | ($h^{-1}$) | $H_2$/MAC | % BDO | % THF | % GBL | % BuOH | % Other |
| 3.5% Pd/ 3.5% Ag/ 5.3% Re/C | 47 | 1300 | 35.5 | 180 | 3625 | 0.66 | 64 | 53.8 | 36.2 | 4.1 | 4.5 | 1.4 |
| 3.6% Pd/ 5.5% Re/C | 47 | 1300 | 35.5 | 180 | 3625 | 0.66 | 64 | 43.9 | 32.2 | 20.2 | 2.4 | 1.3 |

Average Set Temperature.

276.5 g of 1.5 mmACL40 extrudate was impregnated with 286.4 g of the Pd/Ag/Re solution. The mixture was allowed to stand for 5.75 hours, and then dried overnight in an oven at approximately 120° C.

XRD analysis of this catalyst (after reduction as set forth in Example 4) showed no observable diffraction peaks other than those identified as silver metal, indicating that the palladium containing crystallites which are present are on the average smaller than 5 nm.

Comparative Example B—Prior Art Pd/Ag/Re/C Catalyst Preparation

A Pd/Ag/Re/C catalyst of the type described in U.S. Pat. No. 4,985,572 was prepared. The catalyst contained approximately 3.3 weight percent Pd, 3.2 weight percent Ag, 6.6 weight percent Re on the carbon support. The preparation followed the procedure described in U.S. Pat. No.

4,985,572 (which is characterized by the simultaneous deposition of palladium and silver on the carbon support followed by a high temperature (600° C.) heat treatment), with ammonium perrhenate being used in place of rhenium heptoxide.

24.35 g of palladium nitrate solution (7.7% Pd), and 2.9 g of silver nitrate were dissolved in 100 c.c. of distilled water. 50 g of 1.5 mm ACL40 extrudate was added to the solution and the water was removed at approximately 70° C. using a rotary evaporator. The Pd/Ag/ACL40 was then dried overnight at 120° C. in an oven.

The high temperature heat treatment step was carried out by heating in flowing nitrogen the Pd/Ag/ACL40 as follows:

Room temperature to 600° C. in 8 hours.

Hold at 600° C. for 8 hours.

Cool to room temperature.

5.5 g of ammonium perrhenate was dissolved in 100 c.c. of distilled water. The Pd/Ag/ACL40 was then added to the solution. The water was removed at 70° C. using a rotary evaporator. The Pd/Ag/Re/ACL40 was further dried at 120° C. in an oven overnight.

Example 4—Catalyst Testing

The Pd/Ag/Re/ACL40 catalysts prepared as in Example 3 and Comparative Example B (40 c.c.) were separately charged to 0.5" OD Hasteloy C276 reactors and reduced at atmospheric pressure with 0.5 SLM of hydrogen flowing, using the following temperature ramp: room temperature to 280° C. over 11 hours; then held at 280° C. for 5 hours; cool to room temperature.

Catalyst testing was carried out at 2500 psig with a 35.5 weight percent maleic acid/64.5 weight percent $H_2O$ feed. The data shown in Table 2 below was obtained at 160° C., $H_2$ GHSV=2760 $h^{-1}$, LHSV=0.55 $h^{-1}$, and $H_2$/MAC=65, at −109 hours on-stream. Product selectivities were calculated on a molar $C_4$ basis.

TABLE 2

MALEIC ACID HYDROGENATION AT 2500 PSIG

| Catalyst | SELECTIVITY | | | | | |
|---|---|---|---|---|---|---|
| | % BDO | % THF | % GBL | % BuOH | % PrOH | % Other |
| Example 3 | 73.6 | 16.9 | 1.2 | 7.0 | 0.5 | 0.9 |
| Comp. Example B | 57.0 | 17.4 | 20.8 | 3.0 | 0.3 | 1.5 |

The above data illustrates that the catalyst prepared as set forth in Example 3 selectively produces more 1,4-butanediol and substantially less gamma-butyrolactone than the catalyst of Comparative Example B prepared as taught in U.S. Pat. No. 4,985,572. Further, the total selectivity to 1,4-butanediol and tetrahydrofuran for the Example 3 catalyst (90.5%) greatly exceed the total selectivity to these products for the Comparative Example B catalyst (74.4%).

Example 4 and Comparative Examples C and D

A 3.6 weight percent Pd/3.6 weight percent Ag/3.6 weight percent Re/C catalyst (Example 4) was prepared as set forth in Example 1. This catalyst was compared to two 3 weight percent Pd/3 weight percent Re/C catalysts (Comparative Examples C and D) prepared according to Example 1 of U.S. Pat. No. 4,550,185. (U.S. Pat. No. 4,550,185 did not set forth the calcination medium. Comparative Example C was calcined in air and Comparative Example D was calcined in nitrogen.) Each catalyst was tested in accordance with the procedures set forth in Example 2 with any modifications or variance in operating parameters being as shown in Table 3. The results of the comparison are also shown in Table 3.

TABLE 3

MALEIC ACID HYDROGENATION

| Example | Catalyst | TOS (h) | Press. (psig) | [MAC] | Temp (°C.) | LHSV ($h^{-1}$) | $H_2$/MAC | Selectivity | | | |
|---|---|---|---|---|---|---|---|---|---|---|---|
| | | | | | | | | % BDO | % THF | % GBL | % BuOH |
| 4 | 3.6% Pd/ | 46.70 | 1300 | 23 | 178 | 0.60 | 64 | 50.76 | 39.40 | 4.34 | 4.25 |
| | 3.6% Ag/ 3.6% Re/C | 51.00 | 1300 | 23 | 180 | 0.60 | 64 | 41.41 | 51.54 | 1.13 | 4.60 |
| C | 3% Pd/ | 31.70 | 1300 | 23 | 175 | 0.65 | 64 | 15.33 | 76.10 | 1.51 | 6.07 |
| | 3% Re/C | 49.90 | 1300 | 23 | 175 | 0.65 | 64 | 29.08 | 60.21 | 5.49 | 4.22 |
| | | 69.30 | 1300 | 23 | 175 | 0.65 | 64 | 28.97 | 57.89 | 6.65 | 4.55 |
| | | 89.00 | 1300 | 23 | 175 | 0.65 | 64 | 24.18 | 60.75 | 8.39 | 4.57 |
| D | 3% Pd/ | 34.66 | 1300 | 23 | 175 | 0.65 | 64 | 8.34 | 71.33 | 12.27 | 5.89 |
| | 3% Re/C | 58.66 | 1300 | 23 | 175 | 0.42 | 64 | 7.75 | 80.70 | 0.13 | 9.70 |
| | | 81.16 | 1300 | 23 | 170 | 0.65 | 64 | 13.44 | 45.04 | 36.51 | 3.70 |
| | | 104.40 | 1300 | 23 | 170 | 0.65 | 64 | 13.44 | 46.47 | 35.89 | 3.22 |

The data in Table 3 illustrates that a catalyst prepared by the process of the instant invention is more selective to the production of 1,4-butandiol while minimizing the production of gamma-butyrolactone compared to prior art catalysts which do not contain silver (Ag) and are prepared differently which are highly selective to the production of tetrahydrofuran.

It is to be understood that the subject invention is not to be limited by the examples set forth herein. These have been provided merely to demonstrate operability, and the selection of catalysts, metal sources, carbon supports, concentrations, contact times, solids loadings, feedstocks, reaction conditions, and products, if any, can be determined from the total specification disclosure provided, without departing from the spirit of the invention herein disclosed and described, the scope of the invention including modifications and variations that fall within the scope of the attached claims.

We claim:

1. A process for the production of tetrahydrofuran and 1,4-butanediol comprising catalytically hydrogenating a hydrogenatable precursor in contact with a hydrogen-containing gas and a hydrogenation catalyst comprising palladium, silver and rhenium on a carbon support to produce a product comprising a major portion of 1,4-butanediol wherein the hydrogenation catalyst is prepared by the steps of (i) impregnating the carbon support with a source of palladium, silver and rhenium in one or more impregnation steps comprising contacting the carbon support with a source of palladium, silver and rhenium, said palladium, silver and rhenium being in at least one solution;

(ii) drying the impregnated carbon support to remove solvent after each impregnation step; and (iii) heating the impregnated carbon support at a temperature of about 100° C. to about 350° C. under reducing conditions.

2. The process of claim 1 wherein the hydrogenatable precursor is selected from the group consisting of maleic acid, maleic anhydride, fumaric acid, succinic anhydride, succinic acid, dimethyl succinate, gamma-butyrolactone and mixtures thereof.

3. The process of claim 2 wherein the hydrogenatable precursor is maleic acid, maleic anhydride, succinic acid, succinic anhydride or mixtures thereof.

4. The process of claim 1, wherein the scource of palladium is palladium nitrate.

5. The process of claim 2, wherein the source of silver is silver nitrate.

6. The process of claim 2, wherein the source of rhenium is perrhenic acid.

7. The process of claim 1, wherein the palladium, silver and rhenium sources are combined into a single solution and palladium, silver and rhenium are deposited on the carbon support in a single impregnation step.

8. The process of claim 1, wherein the hydrogenation catalyst comprises about 0.1 to about 20 weight percent palladium, about 0.1 to about 20 weight percent silver and about 0.1 to about 20 weight percent rhenium.

9. The process of claim 8, wherein the hydrogenation catalyst comprises about 2 to about 8 weight percent palladium, about 1 to about 8 weight percent silver and about 1 to about 10 weight percent rhenium.

10. The process of claim 1, wherein the palladium is present in the form of palladium containing crystallites having an average size of less than 10 nm.

11. The process of claim 10, wherein the palladium is present in the form of palladium containing crystallites having an average size of less than about 5 nm.

12. The process of claim 1, wherein the ratio of hydrogen to hydrogenatable precursor is between about 5 to 1 and about 1000 to 1.

13. The process of claim 1, wherein the hydrogen-containing gas pressure is between about 20 and 400 atmospheres.

14. The process of claim 1, wherein the process is at a temperature of between about 50° C. and about 350° C.

15. The process of claim 14, wherein the process is at a temperature of between about 100° C. and about 300° C.

16. The process of claim 1, wherein the drying temperature of the impregnated carbon support is between about 80° C. and about 150° C.

* * * * *